United States Patent [19]
Bloomer

[11] Patent Number: 5,647,838
[45] Date of Patent: Jul. 15, 1997

[54] CAMERA FIXTURE FOR STEREOSCOPIC IMAGERY AND METHOD OF USING SAME

[76] Inventor: William E. Bloomer, 585 Bellefontaine St., Pasadena, Calif. 91105

[21] Appl. No.: 570,481

[22] Filed: Dec. 11, 1995

Related U.S. Application Data

[63] Continuation-in-part of Ser. No. 239,872, May 10, 1994, Pat. No. 5,474,519.

[51] Int. Cl.$^6$ ........................................... A61B 1/00
[52] U.S. Cl. ........................ 600/111; 600/102; 206/316.2
[58] Field of Search ..................................... 600/101, 102, 600/111, 160, 166; 348/45; 206/363, 438, 443, 485, 483, 316.1, 316.2, 316.3

[56] References Cited

U.S. PATENT DOCUMENTS

| | | | |
|---|---|---|---|
| 4,386,602 | 6/1983 | Sheldon et al. | 600/102 |
| 4,651,201 | 3/1987 | Schoolman | 600/111 |
| 4,784,117 | 11/1988 | Mayazaki | 600/114 |
| 4,834,518 | 5/1989 | Barber | 600/165 |

*Primary Examiner*—Richard J. Apley
*Assistant Examiner*—John P. Leubecker
*Attorney, Agent, or Firm*—Fulwider Patton Lee & Utecht, LLP

[57] ABSTRACT

The steps of selecting a hand held endoscope holder includes providing distally convergent tubular devices for receipt of the probes of respective endoscopes, securing such endoscopes in fixed relation within such holder converging distally toward one another at a predetermined angle, coupling such endoscopes through respective cameras and power sources to a multiplexer, coupling such multiplexer to a television monitor, fixing the cameras to a fixture to hold them relative to one another for viewing through three dimensional viewing glasses. The holder carrying such endoscopes is then inserted through an incision to transit the respective images of such endoscopes viewed from the respective relative angles of the endoscopes through such cameras, power source and multiplexer to the television monitor for viewing through such glasses.

18 Claims, 6 Drawing Sheets

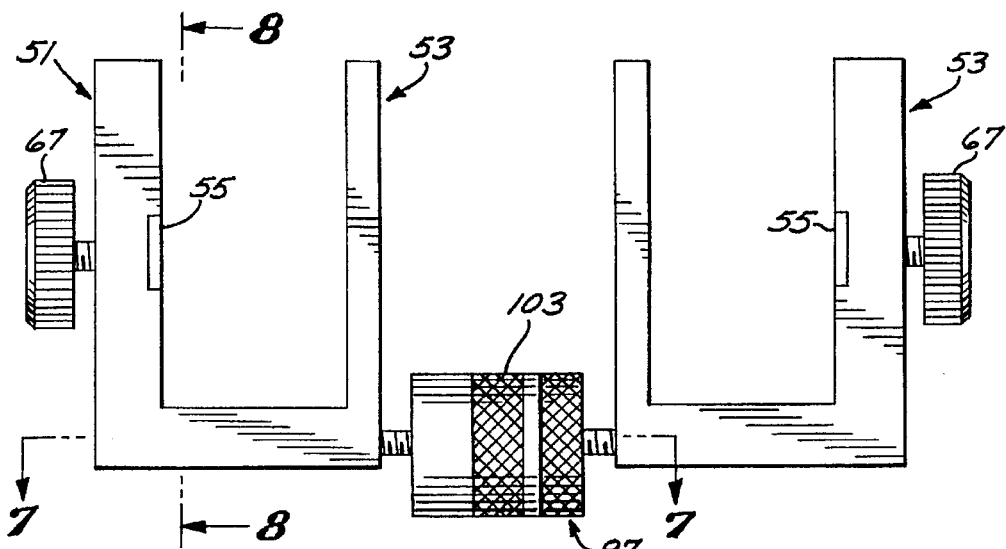
FIG. 6
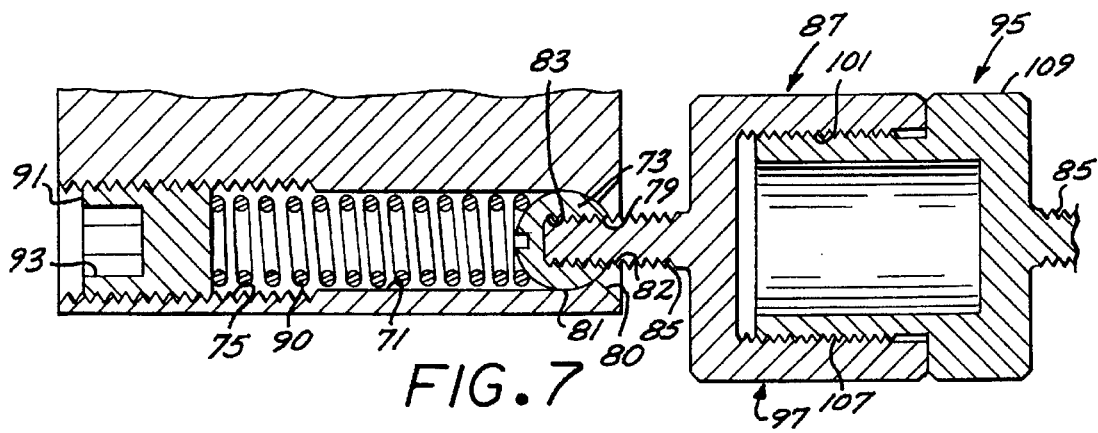
FIG. 7
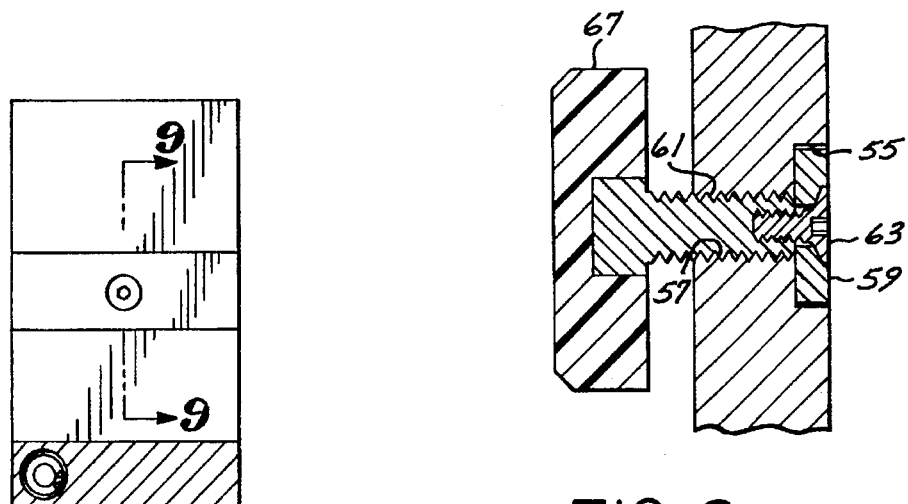
FIG. 8
FIG. 9

CAMERA FIXTURE FOR STEREOSCOPIC IMAGERY AND METHOD OF USING SAME

This is a continuation-in-part of application Ser. No. 08/239,872 filed on May 10, 1994, now U.S. Pat. No. 5,474,519.

BACKGROUND OF THE INVENTION

1. Field of the Invention

The present invention relates to a method and apparatus for holding cameras used for stereoscopic viewing of a patient's body cavity.

2. Description of the Prior Art

Endoscopes have commonly been utilized in surgery to enable the surgeon to view the body cavity through relatively small incisions thereby minimizing trauma and post operative pain and recovery.

Conventional endoscopes typically provide for viewing the internal organs in the form of a planar object without a three dimensional view thus limiting the effectiveness, efficiency and convenience for the surgeon in achieving the objective of the operation. The advantages attendant stereoscopic viewing of a patient's internal organs through a small incision have long been known. The recognition of these advantages have led to the development of various sophisticated methods and equipment in effort to devise an endoscopic probe for insertion through a small incision into a body cavity to enable the surgeon to view the surgery by three dimensional television. However, the devices proposed for such endoscopic systems are typically technically sophisticated requiring significant development costs and capital investment beyond the financial capability of many of the present day medical institutions. Thus, surgeons on the staff of the majority of such institutions are currently left without the capability of performing endoscopic surgery with the benefit of stereoscopic observation of the surgery site.

Substantial work has been performed in the field. It has been proposed to provide a binocular endoscope housed in a tube combined with a conduit for irrigation and including a gear mechanism for rotating an optical shaft within the tube. A device of this type is shown in U.S. Pat. No. 4,061,135 to Widran. The system disclosed is rather sophisticated, expensive and fails to incorporate video cameras and monitors enabling effective use of existing non-stereoscopic endoscopes in any combination which will achieve a perspective view of the surgical site.

It has been proposed to provide a custom made stereoscopic endoscope housed in a sheath bundling a pair of image guides, a light guide and various other channels for air, water, gas or other liquids. A device of this type is shown in U.S. Pat. No. 4,651,201 to Schoolman. While recognizing the advantages of stereoscopic endoscopes, the devices described is relatively complicated, cumbersome, expensive to manufacture and inconvenient to use.

It has also been proposed to provide a arthroscope for viewing of human or animal joints which includes a prism arrangement in effort to achieve stereoscopic capability. A device of this type is shown in U.S. Pat. No. 4,924,853 to Jones. A device of this type requires relatively sophisticated technology and is expensive to manufacture.

Other efforts to provide a stereoscope endoscope device includes the proposal of a pair of flexible endoscopes incorporated in a pair of fiber optical systems to be viewed through oculars. A device of this type is shown in U.S. Pat. No. 3,520,587 to Tasaki. While providing certain benefits, such a device suffers the shortcoming that it is expensive to manufacture and compromises the advantages of rigidity in endoscopes for manipulation in a body cavity.

Other efforts to achieve stereoscopic viewing of internal organs includes the provision of a sophisticated flashing strobe lamp with a synchronized rotating prism as shown in U.S. Pat. No. 4,862,873 to Yajima and an electronic endoscopic device as shown in U.S. Pat. No. 4,926,257 to Miyazaki.

Efforts to stereoscopically view a surgical procedure has led to a proposal of an orbiting fixture indexed to a patient's skull to mount a micro manipulator in fixed relation to the skull with a pair of converging tubes for telescopical receipt of endoscopes to converge together within a distal barrel configured at its distal end with flexible expander fingers to maintain the tissue to be examined spaced from the ends of the endoscopes. A device of this type is shown in U.S. Pat. No. 4,386,602 to Sheldon. Devices of this type, while satisfactory for the precision work required for cranial access, suffer the shortcoming that they are expensive to manufacture and require some degree of expertise to make effective use thereof and are time consuming to set up and use. Moreover, such devices leave the distal ends of the endoscope and associated cameras supported only in cantilever fashion, without fixing the cameras in spaced relation to one another. This then will often result in relative movement between the cameras thus tending to cause relative movement between the endoscopes and consequent relative movement between the images displayed on a monitor thereby contributing to the challenge of performing the surgical procedure in an efficient and safe manner.

The general thinking of current day manufacturers of stereoscopic thoracoscopes aims at miniaturization for introduction of a probe through a single small incision. Manufacturers such as Zeiss and Baxter have proposed such thoracoscopic systems and, when FDA approval is achieved, each such system may well require a capital investment of $40,000.00 to $50,000.00. Thus, there exists a need for a practical and inexpensive stereoscopic endoscopic apparatus which will make the benefits of stereoscopic viewing available to a wider range of medical institutions and to surgeons practicing in less affluent geographic areas.

In my U.S. Pat. No. 5,475,519, issued Dec. 12, 1994, I disclosed a holder for holding monoscopic endoscopes connected with respective cameras for viewing of a surgical procedures. While satisfactory for its intended purpose, I have discovered that performance of that apparatus can be improved by providing a fixture for holding the cameras in fixed relation to one another to thereby provide stability against relative movement during the procedure.

Other objects and features of the invention will become apparent from consideration of the following description taken in conjunction with the accompanying drawing.

BRIEF DESCRIPTION OF THE DRAWINGS

FIG. 6 is a transverse sectional view, in enlarged scale, taken along the line 6—6 of FIG. 5;

FIG. 7 is a horizontal sectional view, in enlarged scale, taken along the line 7—7 of FIG. 6;

FIG. 8 is a vertical sectional view taken along the line 8—8 of FIG. 6; and

FIG. 9 is a sectional view, in enlarged scale, taken along the line 9—9 of FIG. 8.

DESCRIPTION OF THE PREFERRED EMBODIMENT

Figure 1:
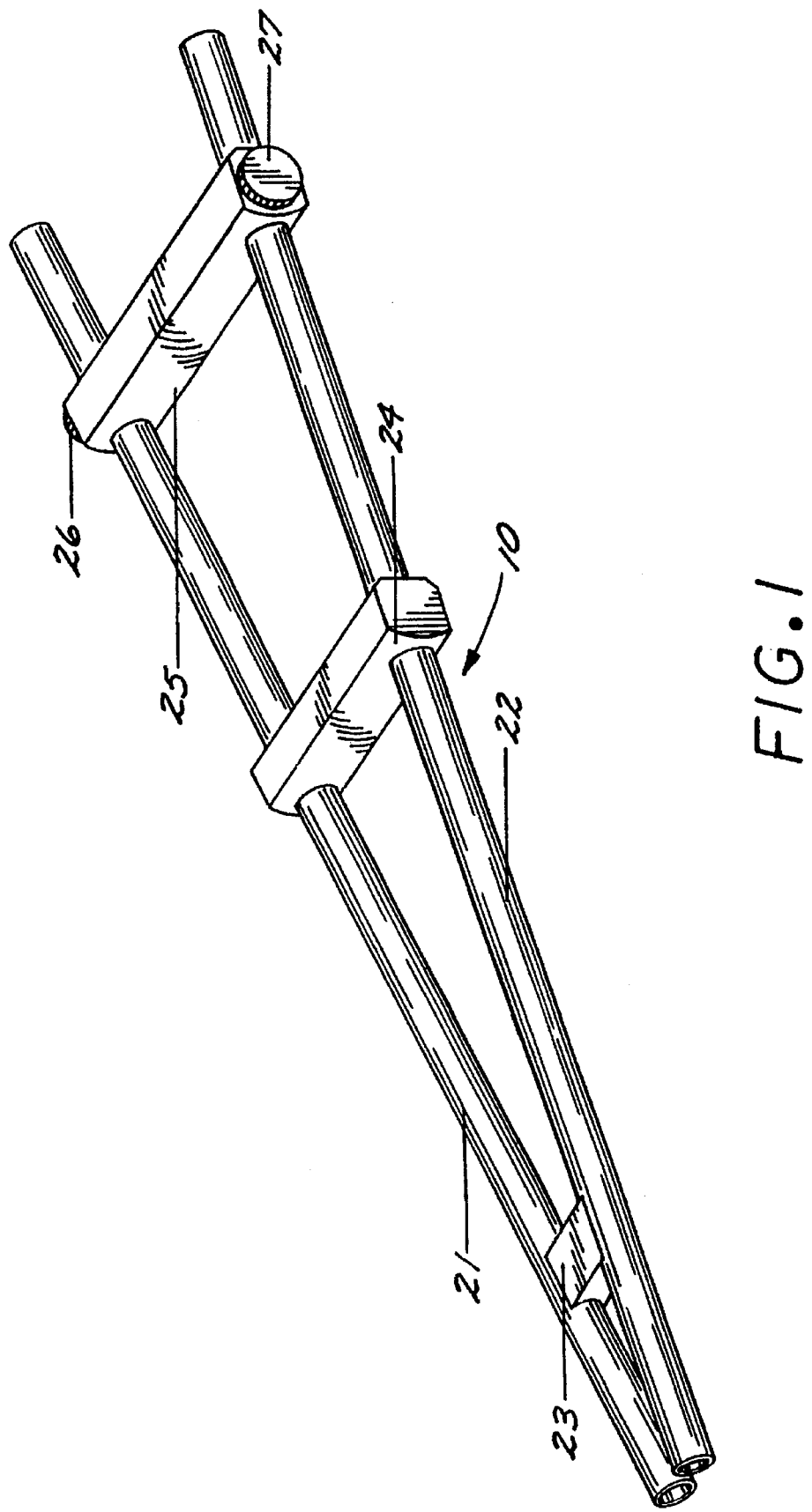
FIG. 1 is a perspective view of a stereoscopic endoscope holder apparatus which can be employed with the present invention.
Figure 2:
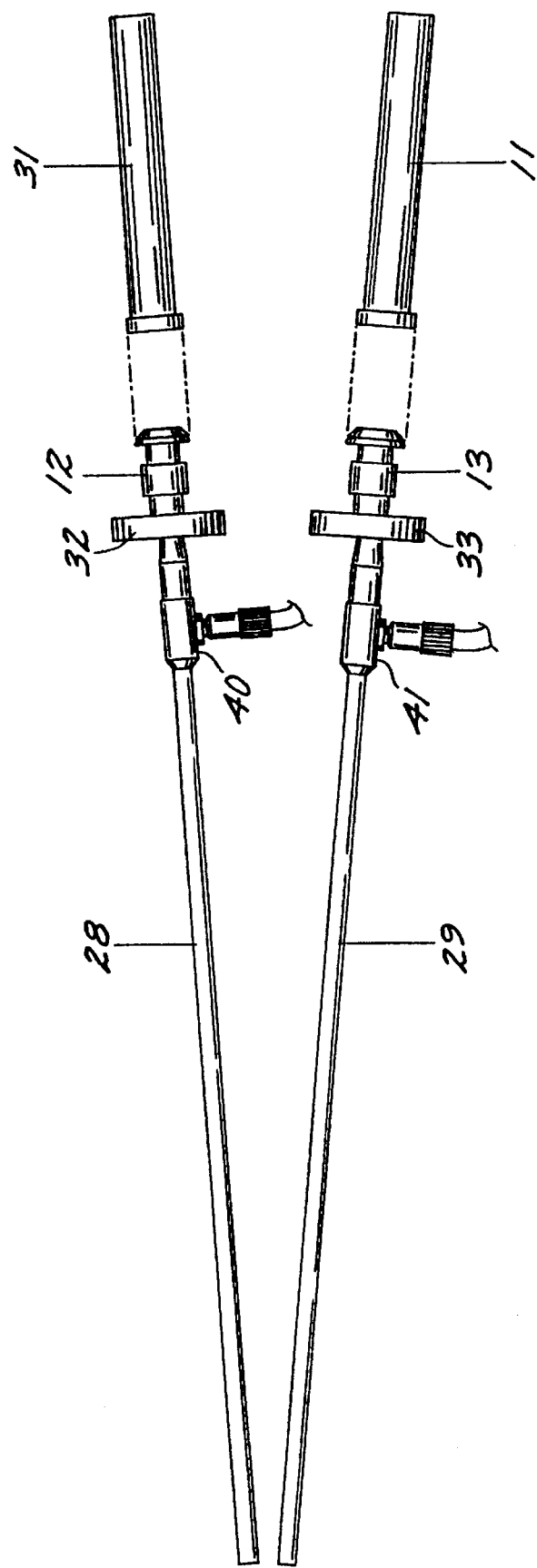
FIG. 2 is a top plan view of endoscopes and cameras which may be utilized with the holder shown in FIG. 1.
Figure 3:
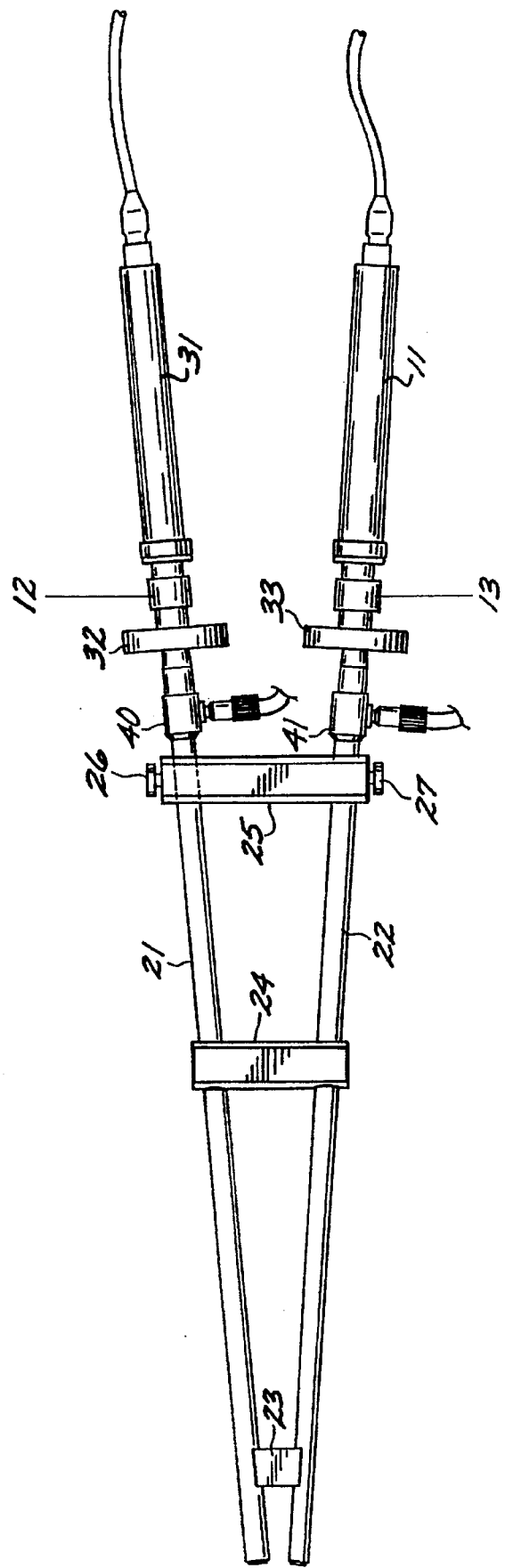
FIG. 3 is a top plan view, in reduced scale, of the endoscope holder shown in FIG. 1 with the endoscope inserted.
Figure 4:
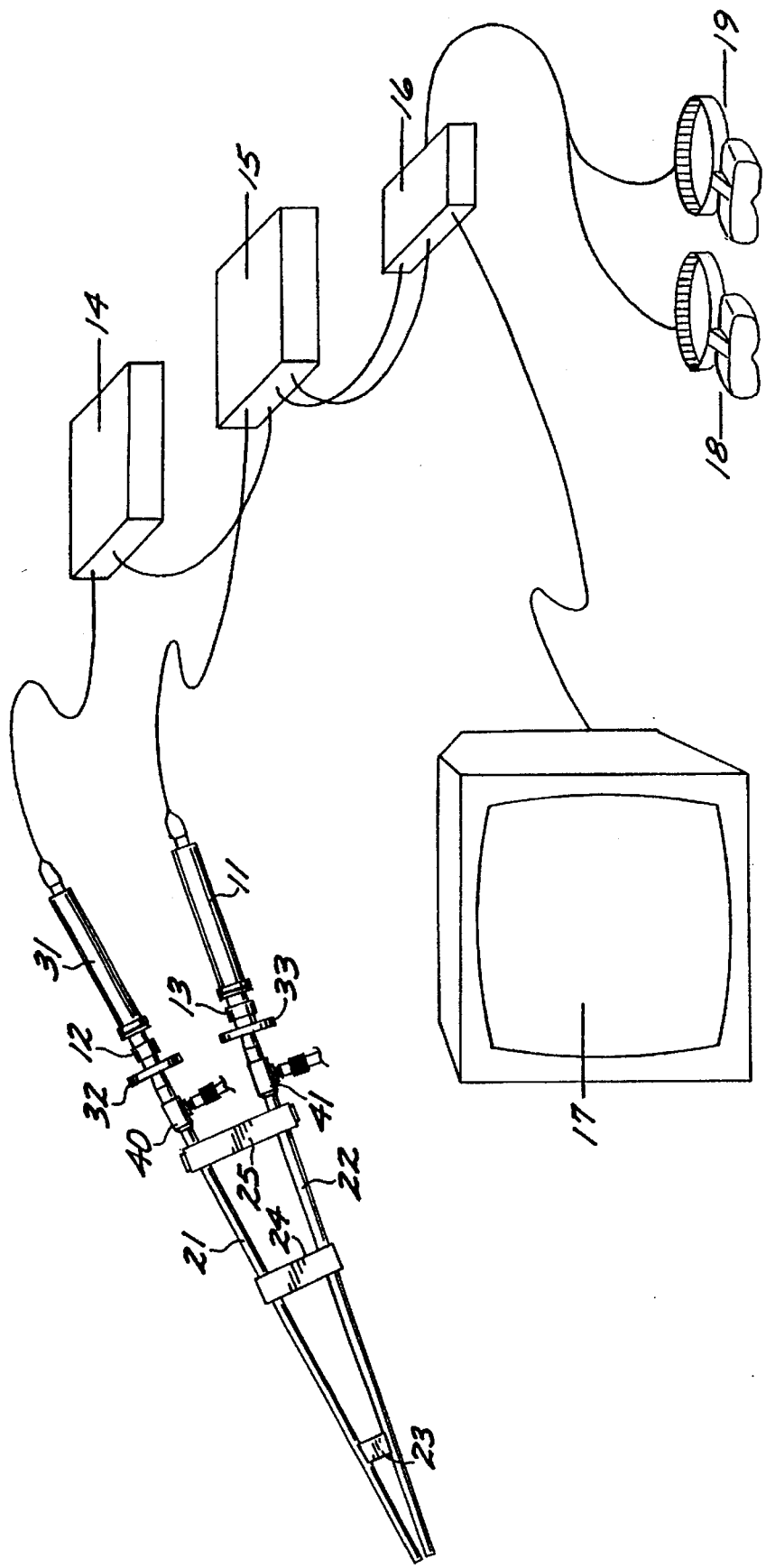
FIG. 4 is a diagrammatic view showing a system incorporating the stereoscopic endoscope holder shown in FIG. 1 but depicted in reduced scale.

Referring to FIGS. 1, 2 and 4, the method of the present invention involves an endoscope holder, generally designated 10, including distally converging open ended stainless steel tubes 21 and 22 carried on a frame and locked in position by means of respective thumb screws 26 and 27. The method involves fixedly securing respective endoscopes 28 and 29 in fixed telescopical relation within the respective tubes 21 and 22 for fixing the respective optical axes thereof in fixed converging angular relationship. The endoscopes may then be coupled through a multiplexer 16 (FIG. 4) to a television monitor 17 for viewing through respective pairs of three dimensional goggles 18 and 19.

Figure 5:
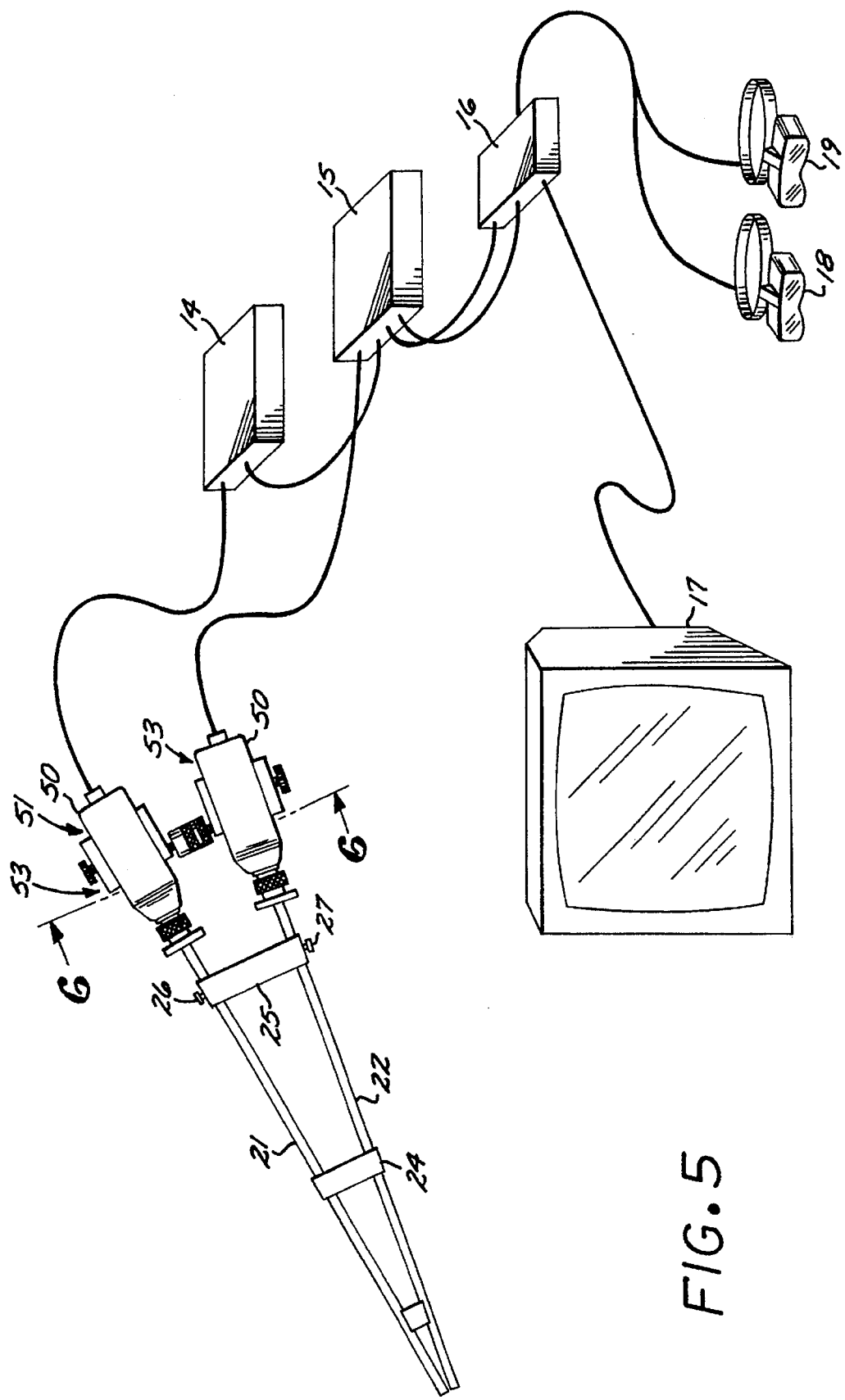
FIG. 5 is a perspective view of the camera fixture and endoscope holder embodying the present invention.

Referring to FIGS. 4, 5 and 6, in practice, the television cameras 31 and 11 or comparable cameras, generally designated 50, may be coupled to the endoscopes and may be held in relative fixed relationship by means of a camera fixture, generally designated 51. Consequently, the method may employ conventional endoscopes 28 and 29 to be held in the holder 10 with the cameras 50 held fixed so the optical ends of such endoscopes may be inserted through a small incision in a body cavity for three dimensional viewing the surgery site.

With the current high cost of medical care and public consciousness of medical expenses, concern is prevalent over the capital investment by medical institutions. Consequently, many institutions cannot afford or are not in a position to invest the capital required to have access to the latest and most expensive medical equipment to support surgeons in their daily tasks.

It is known that for certain interventional procedures, three dimensional observation of the surgery site is beneficial. While three dimensional endoscopic devices are currently under development and may be available to support endoscopic surgery, such devices are prohibitively expensive for many medical institutions. However, them exists at numerous different institutions the various medical equipment available to perform endoscopic surgery. These institutions already possess the required endoscopes, cameras and television monitors, and the only additional equipment required for three-dimension viewing is that of a multiplexer and appropriate binoculars. This would then enable the performance of endoscopic surgery with the benefit of three dimensional observation provided the endoscopes could be securely positioned in fixed relative relationship to pick up the image at the surgery site and convey it to the three dimensional monitor for viewing by three dimension binoculars. It is thus an object of the present invention to provide a method and apparatus whereby a surgeon might make use of existing endoscopic and viewing equipment already in inventory to enable the performance of endoscopic surgery with the benefit of three dimensional viewing.

To this end, I have provided a framework constructed of three nylon (LP-410) cross bars 23, 24 and 25 of progressively greater length and carrying at their opposite extremities the distally converging open ended endoscopic support tubes 21 and 22. Conventional endoscopes are of tubular construction including a probe with an outside diameter of about 10 m and a length of 31 cm distal to its fiber optic light inlet attachment. Consequently, the endoscopic support tubes 21 and 22 are constructed with an internal diameter of about 11 mm so as to accommodate insertion of a 10 mm scope and a length of about 30.5 cm so as to allow the scope to protrude slightly from the distal end of the holder. It has been determined that the angle at which the optical axes of endoscopes should be positioned in relation to one another to achieve stereoscopic imaging is about 8°. Consequently, the tubes 21 and 22 are carried in the frame bars 23–25 to converge distally together at a relative angle of 8°. As will be apparent to those skilled in the art, it may be desirable to incorporate the endoscopes directly onto the television cameras thus eliminating the more bulky couplers. It may be desirable in construction to reduce somewhat this angle of convergence for the two scope-holding tubes, so as to allow more freedom of manipulation through a small incision.

Referring to FIG. 1, the proximal frame bar 25 is formed at its opposite ends with threaded bores which extend through the exterior walls of the respective tubes 21 and 22 and are configured for receipt of the threaded stems of respective stainless steel thumb screws 26 and 27 which are configured for tightening thereof to press the ends of such threaded stems against endoscopes to be held captive in the respective tubes 21 and 22.

The respective tubes 21 and 22 are configured for telescopical receipt through the internal bore thereof of the stems of conventional 0—degree endoscopes 28 and 29 of the type typically available from Storz or Mueller. These endoscopes are formed near their respective proximal ends with respective flanges 32 and 33 to which may be attached conventional television attachment couplers 12 and 13, respectively, for coupling with respective television cameras 31 and 11. A television camera useful for this purpose is the Sony CCD Color Camera, Model No. 92AXC-99. For coupling such cameras, it has been found that couplers available from Dynamics Coupler, Catalog No. 3344 is useful in that they provide a firm grip on the endoscopes to prevent relative movement and consequent image distortion.

The camera fixture 51, for the purpose of illustration, is shown as a pair of U-shaped cradles 53 (FIG. 6) formed with laterally spaced apart side walls with each outer side wall being formed medially on its interior with a horizontally projecting open ended slot 55 and a centrally disposed through threaded bore 57. Nested in loose fit relationship in the respective slots 55 are respective elongated clamp plates 59 (FIG. 9) carried from the proximate ends of respective threaded clamp screws 61 and connected thereto by means of respective fastener screws 63. The clamp screws 61 carry at their respective distal ends knurled clamp knobs 67.

Referring to FIGS. 6 and 7, the respective cradles 53 are formed in their proximate walls with respective articulation bores 71 formed on their proximal ends with respective semispherical sockets 73 and threaded at their respective distal ends with screw threads 75. Such bores are formed at their proximal ends with respective reduced-in-diameter threaded articulation bores 82 configured proximally with articulation chamfers 80 (FIG. 7) to allow for articulation of such cradles on such balls.

Nested in the respective semi-spherical sockets 73 are articulation balls 81 formed with respective diametrical threaded bore 83 for coupling receipt of the respective threaded shank 85 projecting diametrically from the respective axial end of a cylindrical coupler, generally designated 87.

Referring to FIG. 7, a threaded adjustment plug 91 is screwably received in the distal end of the bore 71 and is formed with an axially opening Allen wrench socket 93. Sandwiched between the respective plugs 91 and balls 81 are respective coil compression springs 90 to exert a bias on the respective balls.

The articulation connector 87 shown for the purposes of illustration includes male and female couplers 95 and 97, respectively. The female coupler 97 is cupped shaped to be formed internally with internal threads 101 and on its peripheral exterior wall with knurling 103. The male connector 95 is formed with a reduced-in-diameter barrel externally threaded at 107 for screwable engagement with the threads 101 and is formed with an enlarged-in-diameter knurled ring 109 for convenient grasping thereof to allow for screwable adjustment of the axial positioning of the male and female couplers to adjust the axial spacing between the cradles 53. In practice, a compression coil spring can be incorporated in the interior of the connector 87 to place a bias on the threads and hold them in frictional engagement and prevent accidental loosening thereof.

Operation of the apparatus of the present invention will now be described. It will be appreciated by those skilled in the art that the apparatus of FIGS. 5–9 operates similar to that for the device of FIGS. 1–4. Accordingly, operation of the devices of FIGS. 1–4 and FIGS. 5–9 will be described together.

Referring to FIG. 4, in practice, the television cameras 31 and 11 are connected with respective power sources 14 and 15. The power sources are then coupled with a conventional multiplexer 16. Useful for this purpose is a multiplexer marketed by T.V. Corp., P.O. Box Q, San Rafael, Calif. 94913 under Model No. 100 as a 12 volt DC stereoscopic multiplexer. The multiplexer is then coupled with a conventional television monitor 17 to provide for three dimensional depth of viewing when observed with the appropriate binoculars. As will be apparent to those skilled n the art, the television monitor 17 may be of the type typically employed for conventional 2-D endoscopy. The goggles 18 and 19 may be three dimensional scope goggles available from Toshiba, Model No. VDG3D1 or those available from Nintendo Famicon and its three dimensional system under Model No. HVG-031. These goggles may be attached by respective electrical leads to the multiplexer. More expensive wireless equipment is available through 3-D TV Corporation, P.O. Box Q, San Rafael, Calif. 94913-4316, if so desired.

It will be appreciated that the endoscope holder of the present invention may be conveniently utilized in performing procedures requiring access to the body cavity in the chest area (thoracoscopy) or in the abdominal area. The holder may be of construction so it can be sterilized by steam autoraving, Steraad sterilization using hydrogen peroxide or sterilization by ethylene oxide. It will be appreciated that the couplers 12 and 13 and cameras 31, 11 and 53 should not be subjected to sterilization to thereby avoid unnecessary deterioration and prolong their useful life. The surgeon may employ the usual technique covering the unsterile cameras and couplers with a sterile sleeve or plastic overlay. The sterile plastic sleeve is attached with sterile tape to the ocular end of each scope and the cameras and couplers with the electrical leads attached is passed carefully down the sterile sleeve without contamination of the exterior thereof. The cameras, screwed securely to the couplers, are clamped to the endoscopes using the clamping mechanism incorporated in the conventional couplers for attachment to the ocular rings of such scopes.

For the configuration disclosed in the preferred embodiment, the endoscopes 28 and 29 may be of the type characterized by a 10 mm, 0° angle and will be held in the tubes 21 and 22 oriented with their axial optical axes at an distally converging angle of 8° to one another. This angle has been found to provide good stereoscopic vision and depth of field. For the configuration shown, the couplers 12 and 13 are spaced apart a distance sufficient to provide a space therebetween for access by the surgeon's fingers to make the necessary rotational adjustment of the respective cameras 31 and 11 and endoscopes 28 and 29. Such endoscopes 28 and 29 typically incorporate respective fiber optic light couplings 40 and 41. While these couplings have been left out of FIG. 5 for clarity, it will be appreciated by those skilled in the art that, in practice, such light couplings will be utilized. It will be appreciated that the endoscopes 28 and 29 may be telescoped to the desired depth in the respective tubes 21 and 22 and that such depth may be limited by engagement of, for instance, the metal arm receptacle for the fiber optic light cord with the proximal ends of the respective tubes. The endoscopes 28 and 29 may be rotated within the tubes 21 and 22 until the desired corresponding parallel, vertical orientation of the images are achieved. The thumb screws 26 and 27 may then be tightened to firmly engage the free ends of the respective stems with the distal extremities of the respective shanks of the endoscopes 28 and 29 to secure them positively in position within the rigid connected tabs 21 and 22 to thus fixedly hold such endoscopes in fixed angular relation to one another.

Referring to FIGS. 5 and 6, in practice, a camera fixture may be installed on the cameras to hold them in positive firm fixed relation. It will be appreciated that the camers 11 and 31 and 50 have some degree of mass thus tending to, when position of the holder is shifted, flex or wiggle the endoscopes thus shifting the optics at the distal end thereby causing relative movement between the two optic axes and consequent blurring or diminishment in definition of the image displayed on the monitor. Consequently, the camera holding fixture 51 may be mounted to the cameras 50 as shown in FIG. 5 to hold such cameras in relative fixed relationship to thereby provide additional support to the proximal ends of the respective endoscopes and thereby minimizing the tendency to impart relative movement to the endoscopes them selves. To overcome this problem, I employ the camera fixture 51. This fixture is installed by adjusting the respective clamp knobs 67 to fully retract the respective clamp plates 59 into the respective clamp slots 55 as shown in FIG. 6. The fixture 51 may then be maneuvered into position beneath the respective cameras 50 and the connector 103 adjusted by rotating the male coupling 95 relative to the female coupling 97 to adjust the approximate lateral spacing between such cradles to accommodate the spacing between the respective cameras 50.

The respective cradles 53 may then be moved upwardly to nest the respective cameras 50 therein and the clamp knob 67 adjusted to press the clamp plates 59 outwardly from their respective slots 55 to engage the confronting side of the respective camera 50 to thereby clamp the camera firmly in position within the respective cradles. Then, any fine adjustment may be completed by further articulation of the respective cradles 53 and consequently cameras 50. It will be appreciated that, if desired, the compression of the coil springs 90 of the clamps may be adjusted by adjusting the respective adjustment plugs 91 to thereby adjust the force on the respective articulation balls 81 and consequent restriction on motion afforded by the frictional resistance formed between the surface of such balls and the nesting sockets 73. Once the subject cradles 53 have been adjusted to rigidly hold the cameras relative to one another, the procedure may proceed for the particular surgery involved.

For thoracoscopy surgery, it will be appreciated that the anesthesiologist will typically insert a double lumen endothrachial tube with one channel clamped off for the purpose of collapsing the lung on the side where the incision is to be made. Similarly, in abdominal use, a diaphragm between the edges of the incision and the scope holder may be required to maintain a volume of air within the abdominal cavity to allow space for manipulation of the holder and visualization of the surgery site. In this regard, it is noted that it is desirable to maintain air pressure within the abdominal cavity to maintain the viscera at a distance from the scope so as to not block visualization of the surgery site. Air leaks around the scopes can be limited or even totally prevented by using a cannula holding device as sold by Conmed Corporation of Utica, N.Y. or possibly a cannula skirt available from Wayne Maxson, 5465 Leitner Drive, West Coral Gables, Fla. 33067.

In any event, for the thoracoscopy surgery the surgeon may make a short incision of about 2—½ or 3 cm long at the appropriate level between the appropriate ribs. The incision then provides access for insertion of the endoscopes 28 and 29 held in the holder 10 without any necessity of spreading the ribs apart As a consequence, postoperative pain experienced by the patient will be minimized. It will be appreciated that, at this stage, the power sources 14 and 15 have been connected to the respective cameras 31 and 11 and input to the multiplexer 16 and the multiplexer outlets connected with the respective three dimensional television monitor 17 and three dimensional goggles 18 and 19. The holder 10 and fixture 51 may then be grasped and extended to the surgery site with the endoscopes 28 and 29 held firmly in relative fixed relationship for stereoscopic viewing of the site. The surgeon and his or her assistant viewing through the goggles 18 and 19 will then have the benefit of three dimensional viewing to thus expedite the surgery time, promote safety and enable the performance of operations which might otherwise be unattainable. These advantages coupled with the decreased operating room time required and the reduction in necessity of capital investment are all advantages attendant applicant's new holder and method.

Typically, the site will be illuminated by fiber optic illumination incorporated in the endoscopes and transmitted through the couplings 40 and 41 (FIG. 4). The respective images will be picked up by the optics of the respective endoscopes to be viewed by the respective cameras 31 and 11 or 50 to be transmitted through the respective power sources 14 and 15 to the multiplexer 16 for multiplexing and transmission of the multiplexed signals to the television monitor and goggles 18 and 19.

It will be appreciated by those skilled in the art that, if desired, the surgeon may initiate the procedure with a single endoscope in the holder 10 and, assuming the procedure goes well, he or she may complete the entire operation with a single endoscope. However, if difficulty should be encountered, it is possible to enlarge the incision slightly to accommodate the holder of the present invention and place in it the original endoscope and then add a second endoscope of identical type to the holder to thereby enable the surgeon to proceed with the benefit of video assisted stereoscopic surgery.

Various modifications and changes may be made with regard to the foregoing detailed description without departing from the spirit of the invention.

What is claimed:

1. A stereoscopic endoscopic holder apparatus for holding a pair of elongated endoscopes projecting from respective cameras spaced apart a predetermined distance to orient the respective optical axes of said endoscopes focused at a predetermined angle converging inwardly toward one another to view a patient's body cavity and comprising:

an endoscope holder including a frame and a pair of tubular devices formed with respective elongated open ended passages converging distally toward one another and configured for receipt of the respective said endoscopes to hold them in fixed relation to one another arranging said endoscopes with the respective optical axes converging at said predetermined angle and adjusters on the respective said tubular devices for holding the respective said endoscopes in the respective said tubular devices;

a camera fixture including a pair of cradles spaced apart and configured to receive the respective said cameras therein, respective clamps for clamping the respective said cameras in the respective said cradles, an articulating connector connected between the respective said cradles to provide for movement of said cradles relative to one another and a restrictor for restricting articulation of said connector whereby said cameras may be nested in said cradles and said clamps tightened thereon and said articulation connector articulated to provide for articulation of said cradles relative to one another for shifting of the relative position of adjustment of the positioning of said endoscopes relative to one another so that said restrictor will then restrict relative movement of said cameras.

2. The apparatus of claim 1 wherein:

said articulation connector includes at least one swivel joint.

3. The apparatus of claim 2 wherein:

said connector includes male and female couplers formed with mating screw threads for relative rotation of said couplers to define said swivel joint.

4. The apparatus of claim 1 wherein:

the respective said cradles are formed with ball sockets; and said connector is formed on its opposite ends with respective balls for rotatable receipt in the respective said sockets.

5. The apparatus claim 4 wherein:

said cradles are formed with respective adjustment bores leading to the respective said sockets; and springs in the respective said bores to bias the respective said balls against the walls of the respective said sockets.

6. The apparatus of claim 4 wherein:

said restrictor includes respective springs for biasing the respective said balls against the walls of the respective said sockets to thereby frictionally resist rotation of said cradles relative to said connector.

7. The apparatus of claim 4 wherein:

said restrictor includes the respective said cradles being formed with threaded bores leading to the respective said sockets and restrictor screws in said restrictor bores for adjustment to exert bearing forces against the respective said balls to restrict movement of the respective said cradles relative to the respective said balls.

8. The apparatus of claim 1 wherein:

said cradles are formed with respective U-shaped frames configured with respective pairs of side walls spaced apart to receive therebetween the respective said cameras and wherein said clamps included threaded bores through at least one of each pair of respective said side walls, said clamps further including clamp adjustment screws screwed through the respective said bores.

9. The apparatus of claim 8 wherein:

the respective said clamps further include respective clamp feet overlying the respective ends of the respective screws.

10. The apparatus of claim 9 wherein:

said connector includes male and female couplers formed with mating screw threads for relative rotation of said couplers to define said swivel joint.

11. An endoscopic camera fixture device for adjustably fixing a pair of endoscopic cameras in side by side relationship relative to one another and comprising:

a camera fixture including a pair of cradles spaced apart and configured to receive the respective said cameras therein;

respective clamps for clamping the respective said cameras in the respective said cradles;

an articulating connector connected between the respective said cradles to provide for movement of said cradles relative to one another; and a restrictor for restricting articulation of said connector whereby said cameras may be nested in said cradles and said clamps tightened thereon and said articulation connector articulated to provide for articulation of said cradles relative to one another for shifting of the relative position of adjustment of the positioning of said endoscopes relative to one another so that said restrictor will then restrict relative movement of said cameras.

12. The apparatus of claim 11 wherein:

said articulation connector includes a swivel joint.

13. The apparatus of claim 12 wherein:

the respective said clamps further include respective clamp feet overlying the respective ends of the respective screws.

14. The apparatus of claim 11 wherein:

said cradles are formed with respective U-shaped frames configured with respective pairs of side walls spaced apart to receive therebetween the respective said cameras and wherein said clamps included threaded bores through at least one of each pair of respective said side walls, said clamps further including clamp screws screwed through the respective said bores.

15. The apparatus of claim 10 wherein:

the respective said cradles are formed with ball sockets; and said connector is formed on its opposite ends with respective balls for rotatable receipt in the respective said sockets.

16. The apparatus of claim 15 wherein:

said restrictor includes respective springs for biasing the respective said balls against the walls of the respective said sockets to thereby frictionally resist rotation of said cradles relative to said connector;

said restrictor includes the respective said balls being sized to form a friction fit with the respective said sockets to thereby frictionally resist rotation of said cradles relative to said connector.

17. A method of stereoscopically observing a tissue in a patient's body cavity involving utilization of a pair of conventional elongated monoscopic endoscopes including elongated optical tubes of a predetermined size and configuration and having respective axial optical axes leading from camera couplers formed at their respective one ends, including the following steps:

selecting a hand held holder including a pair of elongated open ended tubular housings carried by a rigid flame and sized and configured for telescopical receipt of the respective said optical robes of said endoscopes from one end thereof to view out the respective opposite ends thereof, said housings converging towards one another at a predetermined angle from said one ends toward the said respective opposite ends and unobstructed at said opposite ends for close viewing of tissues within said cavity;

sliding said endoscopes into the respective said housings from the respective said one ends to leave the respective said camera couplers accessible;

affixing the respective said endoscopes in fixed relation in the respective said housings;

selecting a pair of cameras and coupling them to the respective said camera couplers;

selecting a camera fixture for mounting the respective cameras from the opposite sides thereof and having an articulating connector to provide for articulation of said cameras relative to one another;

adjusting said articulating connector to adjust the relative position of said cameras and holding said cameras in their adjusted position;

making an incision for access to said body cavity for insertion of said holder and endoscopes;

selecting a multiplexing device;

coupling said multiplexing device to the respective said endoscopes;

selecting a monitor;

coupling said monitor to said multiplexing device for displaying of images from said multiplexing device;

selecting three dimensional viewing glasses for viewing the images on said monitor; and grasping said holder and fixture and inserting the distal extremities of said endoscopes in said holder through said incision to view said tissue through said three dimensional glasses whereby said conventional elongated monoscopic endoscopes may be utilized for stereoscopic viewing of said cavity.

18. A method as set forth in claim 17 involving utilization of a pair of thoracoscopic endoscopes and wherein:

said step of making said incision includes making said incision in said patient's chest adjacent a lung; and further including the steps of selecting thoracoscopic endoscopes as the pair of elongated monoscopic endoscopes; and moving said tissue away by inserting an endotracheal tube and deflating said lung.

* * * * *

UNITED STATES PATENT AND TRADEMARK OFFICE
CERTIFICATE OF CORRECTION

PATENT NO. : 5,647,838
DATED : July 15, 1997
INVENTOR(S) : William E. Bloomer

It is certified that error appears in the above-identified patent and that said Letters Patent is hereby corrected as shown below:

In the ABSTRACT, line 11, delete "transit" and insert --transmit--;

Column 3, line 48, delete "them" and insert --there--;

Column 5, line 56, delete "autoraving" and insert --autoclaving--;

Column 10, line 11, delete "flame" and insert --frame--;

Column 10, line 13, delete "robes" and insert --tubes--.

Signed and Sealed this

Ninth Day of September, 1997

Attest:

BRUCE LEHMAN

*Attesting Officer*     *Commissioner of Patents and Trademarks*